United States Patent
Gullo et al.

(10) Patent No.: US 9,133,286 B2
(45) Date of Patent: Sep. 15, 2015

(54) PRODUCTION OF SUBSTITUTED PHENYLENE DIBENZOATE INTERNAL ELECTRON DONOR AND PROCATALYST WITH SAME

(75) Inventors: Michael F. Gullo, Midland, MI (US); Gary A. Roth, Midland, MI (US); Tak W. Leung, Houston, TX (US); Clark C. Williams, Lake Jackson, TX (US)

(73) Assignee: W. R. Grace & Co.-Conn, Columbia, MD (US)

( * ) Notice: Subject to any disclaimer, the term of this patent is extended or adjusted under 35 U.S.C. 154(b) by 0 days.

(21) Appl. No.: 13/220,910

(22) Filed: Aug. 30, 2011

(65) Prior Publication Data
US 2013/0053525 A1    Feb. 28, 2013

(51) Int. Cl.
| | |
|---|---|
| C07C 69/94 | (2006.01) |
| C07C 67/14 | (2006.01) |
| C07C 309/00 | (2006.01) |
| C08F 10/00 | (2006.01) |
| C08F 110/06 | (2006.01) |
| C08F 210/16 | (2006.01) |

(52) U.S. Cl.
CPC .............. C08F 10/00 (2013.01); C07C 67/14 (2013.01); *C08F 110/06* (2013.01); *C08F 210/16* (2013.01)

(58) Field of Classification Search
None
See application file for complete search history.

(56) References Cited

U.S. PATENT DOCUMENTS

| | | | | |
|---|---|---|---|---|
| 5,156,962 | A * | 10/1992 | Suzuki et al. ................. | 435/135 |
| 5,539,309 | A | 7/1996 | Van Wyk et al. | |
| 5,948,212 | A | 9/1999 | Kilty et al. | |
| 8,507,717 | B2 | 8/2013 | Leung et al. | |
| 2004/0034131 | A1 * | 2/2004 | Chowdhury et al. ......... | 524/155 |
| 2010/0174105 | A1 | 7/2010 | Leung et al. | |
| 2010/0204506 | A1 | 8/2010 | Chen | |
| 2010/0222530 | A1 | 9/2010 | Chen | |

FOREIGN PATENT DOCUMENTS

| | | |
|---|---|---|
| CN | 101318886 | * 12/2008 |
| WO | 2010078512 A2 | 7/2010 |

OTHER PUBLICATIONS

STN abstract of Zhu et al. (CN 101318886).*
English Translation of Zhu et al. (CN 101318886, 2008).*
International Search Report for PCT/US2012/049935, dated Oct. 23, 2012, 3 pgs.
Provisional U.S. Appl. No. 61/468,928, filed Mar. 29, 2011.
Dichloromethane, Chapter 5.7, Printed on Jan. 1, 2015.
New World Encyclopedia, Ethyl Acetate, <http://www.newworldencyclopedia.org/entry/Ethyl_acetate>, Printed on Mar. 23, 2015, 4 pages.
OEHHA Water 2-chlorotoluene, Office of Environmental Health Hazard Assessment, <http://oehha.ca.gov/water/pals/2chlorotol.html>, Printed on Mar. 18, 2015, Copyright 2007, 3 pages.
Wikipedia, "Chlorobenzene", <http://en.wikipedia.org/w/index.php?title=Chlorobenzene&printable=yes>, Printed on Mar. 18, 2015, Last Modified on Feb. 22, 2015, 4 pages.

* cited by examiner

*Primary Examiner* — Sudhakar Katakam
*Assistant Examiner* — Jennifer C Sawyer
(74) *Attorney, Agent, or Firm* — Lerner, David, Littenberg, Krumholz & Mentlik, LLP

(57) ABSTRACT

The present disclosure is directed to the production of substituted phenylene aromatic diesters and 5-tert-butyl-3-methyl-1,2-phenylene dibenzoate (or "BMPD") in particular. The processes disclosed herein produce a liquid BMPD product. The liquid BMPD product unexpectedly creates production efficiencies by reducing the number of production steps, reducing the amount and/or number of reagents required for BMPD production. The liquid BMPD product may also be utilized in procatalyst production yielding similar production efficiencies. The procatalyst composition is subsequently used for olefin polymerization.

13 Claims, 5 Drawing Sheets

US 9,133,286 B2

PRODUCTION OF SUBSTITUTED PHENYLENE DIBENZOATE INTERNAL ELECTRON DONOR AND PROCATALYST WITH SAME

BACKGROUND

The present disclosure relates to the production of substituted phenylene aromatic diesters, procatalysts containing same, and polymers produced with the procatalysts.

Substituted phenylene aromatic diesters are used as internal electron donors in the preparation of procatalyst compositions for the production of olefin-based polymers. In particular, Ziegler-Natta catalysts containing 5-tert-butyl-3-methyl-1,2-phenylene dibenzoate as internal electron donor show high catalyst activity and high selectivity during polymerization. In addition, such catalysts produce olefin-based polymer (such as propylene-based polymer) with high isotacticity and medium to broad molecular weight distribution.

The art recognizes the need for olefin-based polymers and propylene-based polymers with improved properties. Desired are multiple and/or alternate synthesis pathways for the production of substituted phenylene aromatic diester to ensure a cost-effective, and reliable supply of the same.

SUMMARY

The present disclosure is directed to the production of substituted phenylene aromatic diesters and 5-tert-butyl-3-methyl-1,2-phenylene dibenzoate (or "BMPD") in particular. The BMPD is subsequently utilized as an internal electron donor in the synthesis of a procatalyst composition. The resultant procatalyst composition is used for the polymerization of olefin-based polymer. The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

A precursor, namely 5-tert-butyl-3-methylcatechol, is used in the production process. The present processes simplify production of the BMPD, and/or simplify the production of the procatalyst composition yielding economic savings, a reduction in production resources (reduction in energy, equipment, manpower, and/or production reagents). These advantages promote large-scale and efficient production of (1) BMPD, (2) procatalyst composition with BMPD, and (3) olefin polymer with BMPD.

The present disclosure provides a process. In an embodiment, a process is provided and includes combining, under reaction conditions in a reaction mixture, 5-tert-butyl-3-methyl catechol (BMC), triethylamine, benzoyl chloride, and a water insoluble solvent. The process also includes forming a liquid 5-tert-butyl-3-methyl-1,2-phenylene dibenzoate (BMPD) product in the reaction mixture.

In an embodiment, the water insoluble solvent is selected from toluene, ethyl acetate, chlorobenzene, orthochlorotoluene, and combinations thereof.

The present disclosure provides another process. In an embodiment, a process is provided an includes combining, under reaction conditions in a first reaction mixture, a water insoluble solvent, BMC, triethylamine, and benzoyl chloride to form a liquid BMPD product. The process includes adding, under reaction conditions, the liquid BMPD product to a second reaction mixture. The second reaction mixture includes a procatalyst precursor, a halogenating agent, and chlorobenzene. The process further includes forming a solid procatalyst composition.

In an embodiment, the water insoluble solvent is selected from toluene, ethyl acetate, orthochlorotoluene, chlorobenzene, and combinations thereof.

The present disclosure provides another process. In an embodiment, a process is provided and includes forming a liquid BMPD product and adding, under reaction conditions, the liquid BMPD product to a procatalyst precursor, a halogenating agent, and chlorobenzene to form a solid procatalyst composition. The process includes contacting an olefin, under polymerization conditions, with the solid procatalyst composition, a cocatalyst, and an external electron donor; and forming an olefin-based polymer.

In an embodiment, the process includes forming the liquid BMPD product in a water insoluble solvent selected from toluene, ethyl acetate, orthochlorotoluene, chlorobenzene, and combinations thereof.

An advantage of the present disclosure is an improved process for the production of 5-tert-butyl-3-methyl-1,2-phenylene dibenzoate (BMPD), a substituted phenylene aromatic diester.

An advantage of the present disclosure is a process for producing BMPD that reduces process steps thereby increasing production efficiency.

An advantage of the present disclosure is the provision of a phthalate-free catalyst composition and a phthalate-free olefin-based polymer produced therefrom.

An advantage of the present disclosure is an improved process for the production of procatalyst composition containing BMPD.

An advantage of the present disclosure is a process for producing procatalyst composition containing BMPD that reduces the number of process steps and/or reduces the number/amount of reagents required to produce the procatalyst composition.

An advantage of the present disclosure is a process for large scale production of BMPD.

An advantage of the present disclosure is an environmentally-safe, non-toxic production process for BMPD.

An advantage of the present disclosure is a simple, time-effective, and/or cost-effective purification process for BMPD.

DETAILED DESCRIPTION

Figure 1:
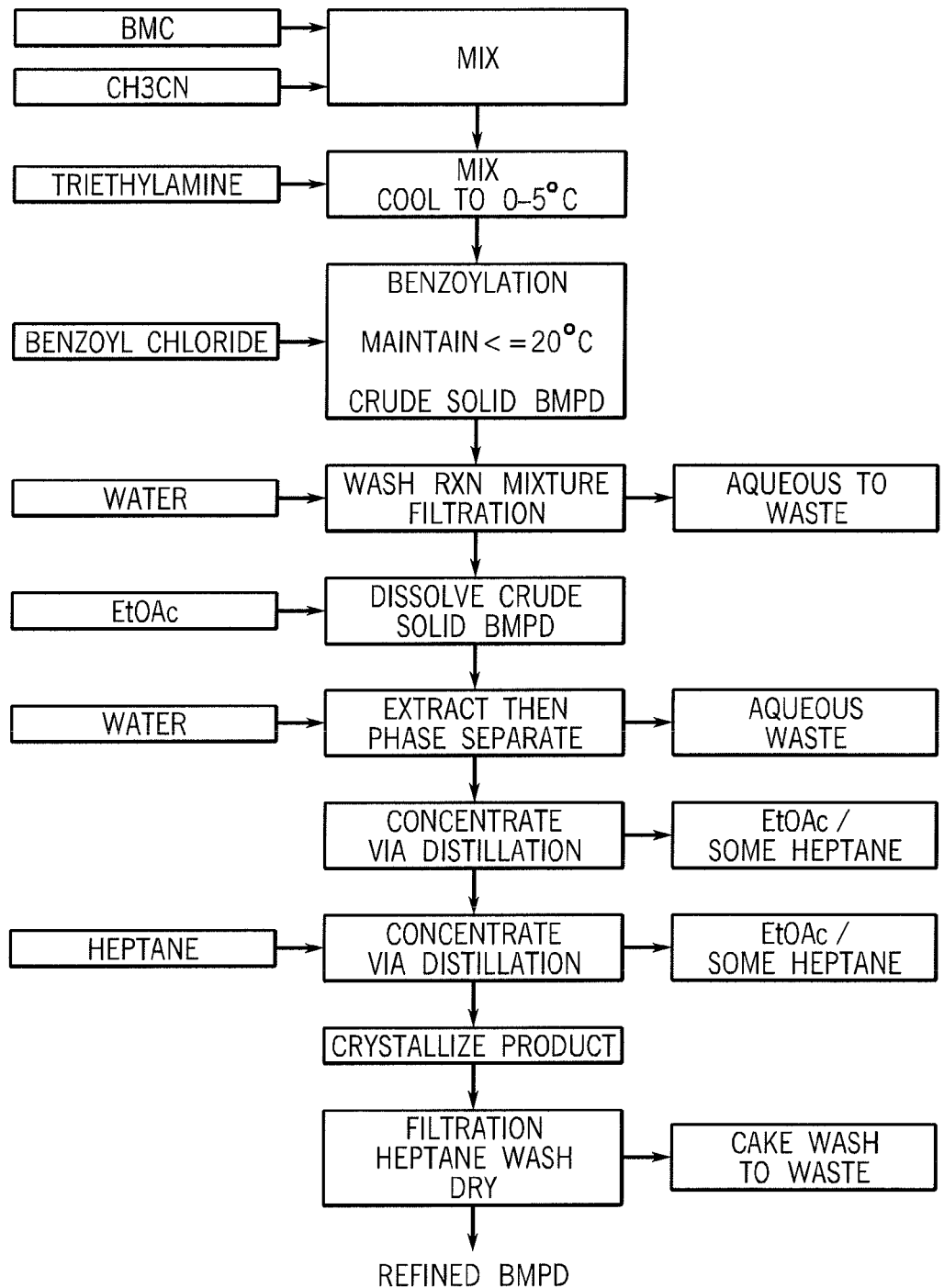
FIG. 1 is a flowchart showing a process for producing BMPD.

The present disclosure is directed to the production of substituted phenylene aromatic diester. The compound 5-tertbutyl-3-methylcatechol (or "BMC") is found to be an effective precursor for the production of the substituted phenylene aromatic diester, 5-tert-butyl-3-methyl-1,2-phenylene dibenzoate (or "BMPD"). BMPD is an effective internal electron donor in Ziegler-Natta catalysts for olefin polymerization. The processes disclosed herein advantageously provide economical (time, resource, production, and monetary economies), simplified, up-scalable, pathways for BMPD synthesis with yields acceptable for commercial/industrial application thereof.

The compound 5-tert-butyl-3-methylcatechol (BMC) has the structure (I) provided below.

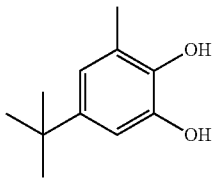

(I)

BMC is an effective precursor in the production of 5-tert-butyl-3-methyl-1,2-phenylene dibenzoate (BMPD). BMPD has the structure (II) provided below.

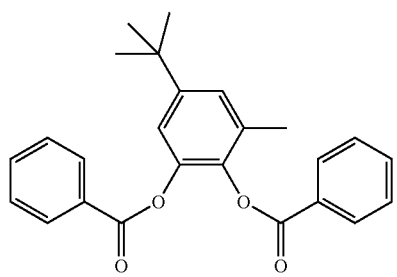

(II)

Synthetic pathways for BMC and BMPD are known. Nonlimiting examples of suitable production for BMC and/or BMPD are provided in U.S. patent application Ser. No. 12/651,142 filed on Dec. 31, 2009 and U.S. patent application No. 61/468,928 filed on Mar. 29, 2011, the entire content of each application incorporated by reference herein.

1. Liquid BMPD Synthesis

The present disclosure provides a process. In an embodiment, a process for producing 5-tert-butyl-3-methyl-1,2-phenylene dibenzoate (BMPD) is provided and includes combining, under reaction conditions in a reaction mixture, 5-tert-butyl-3-methylcatechol (BMC), triethylamine, benzoyl chloride, and a water insoluble solvent. The process further includes forming a liquid BMPD product in the reaction mixture.

As used herein, "reaction conditions," are temperature, pressure, reactant concentrations, solvent concentrations, reactant mixing/addition parameters, and/or other conditions within a reaction vessel that promote reaction between the reagents and formation of the resultant product.

A "water insoluble solvent," as used herein, is a liquid that is immiscible, or substantially immiscible, with water. When mixed with water, the water insoluble solvent phase separates from the water. In an embodiment, the water insoluble solvent has a solubility in water less than 10 g/100 g water at standard temperature and pressure. Nonlimiting examples of suitable water insoluble solvent include toluene, ethyl acetate, orthochlorotoluene, chlorobenzene, and combinations thereof.

The BMC, triethylamine, benzoyl chloride and water insoluble solvent may be added to the reaction vessel in any order as desired. In an embodiment, the BMC is added to the water insoluble solvent in the reaction vessel. Triethylamine is subsequently added and the reaction mixture is cooled to a temperature from 0° C. to 5° C.

In an embodiment, the benzoyl chloride is added to the reaction vessel containing BMC, triethylamine, and the water insoluble solvent. During benzoyl chloride addition, the temperature of the reaction mixture is maintained at less than or equal to 20° C.

The benzoyl chloride reacts with the BMC to form 5-tert-butyl-3-methyl-1,2-phenylene dibenzoate (BMPD). The triethylamine absorbs HCl, a by-product of the reaction. The BMPD is a liquid product in the reaction mixture. In other words, the BMPD is soluble in the water insoluble solvent.

In an embodiment, the process includes adding water to the reaction mixture and washing the liquid BMPD product with the water. The wash is performed by mixing the water with the reaction mixture by way of stirring and/or agitation. The water insoluble solvent is insoluble in the water. Thus, the liquid BMPD product remains dissolved in the water insoluble solvent during the water wash, the BMPD product remaining in the liquid phase. Bounded by no particular theory, addition of the water quenches the reaction, removes contaminants and/or unreacted reagents from the liquid BMPD product and/or the reaction mixture; removes ionic impurities and/or ionic by-products from the liquid BMPD product and/or the reaction mixture; and purifies or otherwise cleanses the liquid BMPD product.

In an embodiment, the process includes separating the liquid BMPD product from the water. The water/reaction mixture combination is a two phase system having an aqueous (water) phase and a nonaqueous phase. The water/reaction mixture combination is allowed to phase separate. The aqueous phase is then removed from the nonaqueous phase. Separation is performed by way of decantation.

In an embodiment, the process includes concentrating the liquid BMPD product, and forming a solid BMPD product. Concentration from a liquid BMPD product to a solid BMPD product may occur by way of filtration, evaporation (roto-evaporation), and combinations thereof.

In an embodiment, the process includes purifying the solid BMPD product. Purification includes hydrocarbon washing (heptane) the solid BMPD product to remove organic by-products/impurities/solvents and optional drying. In an embodiment, the process includes purifying the BMPD, and forming a BMPD composition composed of 98 wt %, or greater than 98 wt %, or greater than 99 wt %, to 99.9 wt % BMPD.

The foregoing process advantageously reduces process steps. Utilization of the water insoluble solvent during BMPD synthesis advantageously eliminates the necessity to isolate and retrieve BMPD precipitate (solid) from the reaction mixture. The present process avoids a solid product in the reaction mixture thereby eliminating the need for retrieval of a crude solid reaction product from the reaction mixture and subsequent dissolution and re-crystallization of the crude product to yield a purified product. The present process yields a liquid BMPD product that is advantageously washed as a liquid. The present process has a single reduction to solid phase, i.e., the concentration step (FIG. 2) or no reduction to solid phase (FIG. 3). Accordingly, the present process requires no dissolution step and/or re-crystallization step. The present process advantageously reduces the number of production steps, reducing production equipment, reducing manhours required to produce the BMPD, and/or reducing the reagents required for BMPD production.

In addition to BMC, the processes disclosed herein may utilize a wide family of substituted catechol as a starting reagent. Catechols suitable as starting reagents in the present processes are catechols substituted at the 4-position, such as 4-methyl catechol and/or 4-tert-butyl catechol which correspondingly produce 4-methyl 1,2-phenylene dibenzoate and 4-tert-butyl 1,2-phenylene dibenzoate. Catechols with other substitution patterns can also be used.

2. Procatalyst Production

The present disclosure provides another process. In an embodiment, a process for producing a procatalyst composition is provided and includes combining, under reaction conditions in a first reaction mixture, a water insoluble solvent, BMC, triethylamine, and benzoyl chloride. The BMC and benzoyl chloride react to form a liquid BMPD product (in the water insoluble solvent) in the first reaction mixture. The process further includes adding, under reaction conditions, the liquid BMPD product to a second reaction mixture. The second reaction mixture includes a procatalyst precursor, a halogenating agent, and optionally chlorobenzene and/or toluene and/or orthochlorotoluene. The process further includes forming a solid procatalyst composition.

In an embodiment, the process includes adding to the first reaction mixture the water insoluble solvent selected from toluene, ethyl acetate, orthochlorotoluene, chlorobenzene, and combinations thereof.

In an embodiment, the process includes adding the water insoluble solvent chlorobenzene to the first reaction mixture.

In an embodiment, the water insoluble solvent in the first reaction mixture and the solvent in the second reaction mixture is chlorobenzene. Having the common solvent chlorobenzene across the first reaction mixture and the second reaction mixture yields production efficiency. Production efficiency occurs because the reaction product, namely the liquid BMPD product, of the first reaction mixture is ready to add to the second reaction mixture without further refinement or processing. The liquid BMPD is a liquid in both the first reaction mixture and the second reaction mixture.

In an embodiment, the second reaction mixture does not include chlorobenzene. Rather, the chlorobenzene from the first reaction mixture is utilized as the solvent in the second reaction mixture.

In an embodiment, the process includes adding the water insoluble solvent orthochlorotoluene to the first reaction mixture.

In an embodiment, the water insoluble solvent in the first reaction mixture is orthochlorotoluene and the solvent in the second reaction mixture is chlorobenzene. The use of orthochlorotoluene (OCT) as the solvent in the first reaction mixture is particularly advantageous because the OCT is subsequently used as a separation agent when recovering the chlorobenzene solvent and $TiCl_4$ of the second reaction mixture and the byproducts formed during chlorination of the procatalyst precursor.

The second reaction mixture includes a procatalyst precursor. The procatalyst precursor is a magnesium moiety compound (MagMo), a mixed magnesium titanium compound (MagTi), or a benzoate-containing magnesium chloride compound (BenMag). In an embodiment, the procatalyst precursor is a magnesium moiety ("MagMo") precursor. The "MagMo precursor" contains magnesium as the sole metal component. The MagMo precursor includes a magnesium moiety. Nonlimiting examples of suitable magnesium moieties include anhydrous magnesium chloride and/or its alcohol adduct, magnesium alkoxide or aryloxide, mixed magnesium alkoxy halide, and/or carboxylated magnesium dialkoxide or aryloxide. In one embodiment, the MagMo precursor is a magnesium di ($C_{1-4}$) alkoxide. In a further embodiment, the MagMo precursor is diethoxymagnesium.

In an embodiment, the procatalyst precursor is a mixed magnesium/titanium compound ("MagTi"). The "MagTi precursor" has the formula $Mg_d Ti(OR^e)_f X_g$ wherein $R^e$ is an aliphatic or aromatic hydrocarbon radical having 1 to 14 carbon atoms or COR' wherein R' is an aliphatic or aromatic hydrocarbon radical having 1 to 14 carbon atoms; each $OR^e$ group is the same or different; X is independently chlorine, bromine or iodine, preferably chlorine; d is 0.5 to 56, or 2 to 4; f is 2 to 116 or 5 to 15; and g is 0.5 to 116, or 1 to 3. The precursors are prepared by controlled precipitation through removal of an alcohol from the reaction mixture used in their preparation. In an embodiment, a reaction medium comprises a mixture of an aromatic liquid, especially a chlorinated aromatic compound, most especially chlorobenzene, with an alkanol, especially ethanol. Suitable halogenating agents include titanium tetrabromide, titanium tetrachloride or titanium trichloride, especially titanium tetrachloride. Removal of the alkanol from the solution used in the halogenation, results in precipitation of the solid precursor, having especially desirable morphology and surface area. Moreover, the resulting precursors are particularly uniform in particle size.

In an embodiment, the procatalyst precursor is a benzoate-containing magnesium chloride material ("BenMag"). As used herein, a "benzoate-containing magnesium chloride" ("BenMag") can be a procatalyst (i.e., a halogenated procatalyst precursor) containing a benzoate internal electron donor. The BenMag material may also include a titanium moiety, such as a titanium halide. The benzoate internal donor is labile and can be replaced by the BMPD or other electron donors during procatalyst and/or catalyst synthesis. Nonlimiting examples of suitable benzoate groups include ethyl benzoate, methyl benzoate, ethyl p-methoxybenzoate, methyl p-ethoxybenzoate, ethyl p-ethoxybenzoate, ethyl p-chlorobenzoate. In one embodiment, the benzoate group is ethyl benzoate. Nonlimiting examples of suitable BenMag procatalyst precursors include catalysts of the trade names SHAC™ 103 and SHAC™ 310 available from The Dow Chemical Company, Midland, Mich. In an embodiment, the BenMag procatalyst precursor may be a product of halogenation of any procatalyst precursor (i.e., a MagMo precursor or a MagTi precursor) in the presence of a benzoate compound.

The second reaction mixture includes a halogenating agent. A "halogenating agent," as used herein, is a compound that converts the procatalyst precursor into a halide form. The second reaction mixture may also include a titanating agent. A "titanating agent," as used herein, is a compound that provides the catalytically active titanium species. Halogenation and titanation convert the magnesium moiety present in the procatalyst precursor into a magnesium halide support upon which the titanium moiety (such as a titanium halide) is deposited.

In an embodiment, the halogenating agent is a titanium halide having the formula $Ti(OR^e)_f X_h$ wherein $R^e$ and X are defined as above, f is an integer from 0 to 3; h is an integer from 1 to 4; and f+h is 4. In this way, the titanium halide is simultaneously the halogenating agent and the titanating agent. In a further embodiment, the halogenating agent is $TiCl_4$ and halogenation occurs by way of chlorination of the procatalyst precursor with the $TiCl_4$. $TiCl_4$ can simultaneously be a chlorinating agent and a titanating agent. The chlorination (and titanation) is conducted in the presence of chlorobenzene, the solvent. In an embodiment, the chlorination (and titanation) are conducted by use of a mixture of 40-60 vol % $TiCl_4$ in chlorobenzene, or 45-55 vol % $TiCl_4$ in chlorobenzene.

The manner in which the procatalyst precursor, the halogenating agent and the BMPD are contacted and/or added to the second reaction mixture may be varied as desired. In an embodiment, the procatalyst precursor is first contacted with a mixture of $TiCl_4$ in chlorobenzene. The resulting mixture is stirred and may be heated if desired. Next, the internal electron donor (the liquid BMPD product) is added to the same reaction mixture without isolating or recovering the procatalyst precursor from the second reaction mixture.

In an embodiment, the procatalyst precursor is contacted with the liquid BMPD product before addition of the $TiCl_4$.

In an embodiment, the procatalyst precursor, the BMPD, and the $TiCl_4$ are added to the second reaction mixture simultaneously or substantially simultaneously.

In the second reaction mixture, the $TiCl_4$ contacts and chlorinates the procatalyst precursor and converts the procatalyst precursor to a solid procatalyst in the presence of the BMPD, the internal electron donor. The $TiCl_4$ converts the magnesium moiety present in the procatalyst precursor into a magnesium chloride support upon which the titanium moiety (such as a titanium halide) is deposited. As used herein, an "internal electron donor" is a compound added during formation of the procatalyst composition, the internal electron donor donating a pair of electrons to one or more metals present in the resultant procatalyst composition. Not wishing to be bound by any particular theory, it is believed that during chlorination the internal electron donor BMPD (1) regulates the position of titanium on the magnesium-based support, (2) facilitates conversion of the magnesium and titanium moieties into respective halides and (3) regulates the crystallite size of the magnesium halide support during conversion. Thus, provision of the BMPD in the second reaction mixture yields a procatalyst composition with enhanced stereoselectivity.

Contact times of the procatalyst precursor with the liquid BMPD are at least 10 minutes, or at least 15 minutes, or at least 20 minutes, or at least 1 hour at a temperature from at least 25° C., or at least 50° C., or at least 60° C. up to a temperature of 150° C., or up to 120° C., or up to 115° C., or up to 110° C.

In an embodiment, the second reaction mixture is heated to a temperature less than 115° C., or from about 90° C. to less than or equal to 100° C. during chlorination. Applicants have surprisingly discovered that chlorination of the procatalyst precursor and the BMPD at a temperature range less than 115° C., and from 90° C. to less than or equal to 100° C. in particular, unexpectedly produces a procatalyst composition with improved selectivity. This result is unexpected because lowering the halogenation temperature during preparation of conventional procatalyst compositions reduces or otherwise diminishes procatalyst selectivity. In particular, it is known that reducing the halogenation temperature below 115° C. during preparation/halogenation of a phthalate-based internal electron donor (such as diisobutylphthalate) diminishes or otherwise degrades the selectivity for the phthalate-based procatalyst composition.

In an embodiment, the process includes adding the first reaction mixture directly to the second reaction mixture. The common solvent (chlorobenzene and/or toluene and/or OCT) across the first reaction mixture and the second reaction mixture advantageously enables the first reaction mixture to be added directly to the second reaction mixture without refinement and/or processing. The common solvent (chlorobenzene and/or toluene and/or OCT) promotes direct and/or immediate transfer of the liquid BMPD product without the need for any intermediate steps. The use of a mixture of solvents can also be advantageous as a solvent mixture may improve increase the efficiency of the $TiCl_4$ and solvent recovery systems/procedures.

The term "directly adding," or "direct addition," or like term as used herein is the addition of the first reaction mixture to the second reaction mixture without any other process steps involving the first reaction mixture. In other words, the first reaction mixture is directly added "as is" to the second reaction mixture.

The chlorination procedure may be repeated one, two, three, or more times as desired, either alone or in the presence of the liquid BMPD. In an embodiment, the resulting solid material (procatalyst material) is recovered from the second reaction mixture and contacted one or more times with additional $TiCl_4$ in the absence (or in the presence) of the additional liquid BMPD product with chlorobenzene as the solvent.

In an embodiment, the process includes second halogenating the solid procatalyst composition with an additional amount of $TiCl_4$, optionally in the presence of additional liquid BMPD product. The solid procatalyst composition may or may not be isolated from the second reaction mixture prior to the second halogenation.

In an embodiment, the process includes third halogenating the solid procatalyst composition with another additional amount of $TiCl_4$, optionally in the presence of the liquid BMPD product. The solid procatalyst composition may or may not be isolated prior to the third halogenation.

The foregoing process(es) convert the procatalyst precursor and the BMPD into a combination of a magnesium moiety and a titanium moiety, into which the BMPD is incorporated. The magnesium moiety is a magnesium chloride. The titanium moiety is a titanium chloride.

After the foregoing one or more halogenation (chlorination) procedures, the resulting solid procatalyst composition is separated from the reaction mixture, by filtering for example, to produce a moist filter cake. The moist filter cake may then be rinsed or washed with a liquid diluent to remove unreacted $TiCl_4$ and may be dried to remove residual liquid, if desired. Typically the resultant solid procatalyst composition is washed one or more times with a "wash liquid," which is a liquid hydrocarbon such as an aliphatic hydrocarbon such as isopentane, isooctane, isohexane, hexane, pentane, or octane. The solid procatalyst composition then can be separated and dried or slurried in a hydrocarbon, especially a relatively heavy hydrocarbon such as mineral oil for further storage or use.

In an embodiment, the resulting solid procatalyst composition has a titanium content of from about 1.0 percent by weight to about 6.0 percent by weight, based on the total solids weight, or from about 1.5 percent by weight to about 4.5 percent by weight, or from about 2.0 percent by weight to about 3.5 percent by weight. The weight ratio of titanium to magnesium in the solid procatalyst composition is suitably between about 1:2 and about 1:160, or between about 1:2.5 and about 1:50, or between about 1:3 and 1:30, or 1:3.5. In an embodiment, the BMPD may be present in the procatalyst composition in a molar ratio of BMPD to magnesium of from about 0.005:1 to about 1:1, or from about 0.01:1 to about 0.4:1. Weight percent is based on the total weight of the procatalyst composition.

In an embodiment, the molar ratio of BMPD to Mg is 0.06:1.

Not wishing to be bound by any particular theory, it is believed that (1) further halogenation by contacting the previously formed solid procatalyst composition with additional titanium chloride, and/or (2) further washing the previously formed procatalyst composition with chlorobenzene at an elevated temperature (100° C.-150° C.), results in desirable modification of the procatalyst composition, possibly by removal of certain inactive or undesired metal compounds that are soluble in the foregoing solvent.

The present process for producing a procatalyst composition may comprise two or more embodiments disclosed herein.

3. Polymerization

Any of the foregoing procatalyst compositions may be used in an olefin polymerization process. In an embodiment, a polymerization process is provided and includes contacting, under polymerization conditions, the procatalyst composition BMPD, a cocatalyst, optionally an external electron donor with propylene and optionally one or more olefins. The polymerization forms a propylene-based polymer (propylene homopolymer) having less than 6 wt %, or less than 4 wt %, or less than 3 wt %, or less than 2.5 wt %, or less than 1 wt %, or from 0.1 wt % to less than 4 wt %, or from 0.1 wt % to less than 2.5 wt % xylene solubles (XS). Weight percent XS is based on the total weight of the polymer.

As used herein, a "cocatalyst" is a substance capable of converting the procatalyst to an active polymerization catalyst. The cocatalyst may include hydrides, alkyls, or aryls of aluminum, lithium, zinc, tin, cadmium, beryllium, magnesium, and combinations thereof. In an embodiment, the cocatalyst is a hydrocarbyl aluminum compound represented by the formula $R_nAlX_{3-n}$, wherein n=1 2, or 3, R is an alkyl, and X is a halide or alkoxide. In an embodiment, the cocatalyst is selected from trimethylaluminum, triethylaluminum, triisobutylaluminum, and tri-n-hexylaluminum.

Nonlimiting examples of suitable hydrocarbyl aluminum compounds are as follows: methylaluminoxane, isobutylaluminoxane, diethylaluminum ethoxide, diisobutylaluminum chloride, tetraethyldialuminoxane, tetraisobutyldialuminoxane, diethylaluminum chloride, ethylaluminum dichloride, methylaluminum dichloride, dimethylaluminum chloride, triisobutylaluminum, tri-n-hexylaluminum, diisobutylaluminum hydride, di-n-hexylaluminum hydride, isobutylaluminum dihydride, n-hexylaluminum dihydride, diisobutylhexylaluminum, isobutyldihexylaluminum, trimethylaluminum, triethylaluminum, tri-n-propylaluminum, triisopropylaluminum, tri-n-butylaluminum, tri-n-octylaluminum, tri-n-decylaluminum, tri-n-dodecylaluminum, diisobutylaluminum hydride, and di-n-hexylaluminum hydride.

In an embodiment, the cocatalyst is triethylaluminum. The molar ratio of aluminum to titanium is from about 5:1 to about 500:1, or from about 10:1 to about 200:1, or from about 15:1 to about 150:1, or from about 20:1 to about 100:1. In another embodiment, the molar ratio of aluminum to titanium is about 45:1.

As used herein, an "external electron donor" (or "EED") is a compound added independent of procatalyst formation and includes at least one functional group that is capable of donating a pair of electrons to a metal atom. Bounded by no particular theory, it is believed that provision of one or more external electron donors in the catalyst composition affects the following properties of the formant polymer: level of tacticity (i.e., xylene soluble material), molecular weight (i.e., melt flow), molecular weight distribution (MWD), melting point, and/or oligomer level.

In an embodiment, the EED is a silicon compound having the general formula (II):

$$SiR_m(OR')_{4-m} \qquad (II)$$

wherein R independently each occurrence is hydrogen or a hydrocarbyl or an amino group, optionally substituted with one or more substituents containing one or more Group 14, 15, 16, or 17 heteroatoms. R contains up to 20 atoms not counting hydrogen and halogen. R' is a $C_{1-20}$ alkyl group, and m is 0, 1, 2, or 3. In an embodiment, R is $C_{6-12}$ aryl, alkyl or alkylaryl, $C_{3-12}$ cycloalkyl, $C_{3-12}$ branched alkyl, or $C_{3-12}$ cyclic amino group, R' is $C_{1-4}$ alkyl, and m is 1 or 2.

In an embodiment, the silane composition is dicyclopentyldimethoxysilane (DCPDMS), methylcyclohexyldimethoxysilane (MChDMS), or n-propyltrimethoxysilane (NPTMS), and any combination thereof.

The polymerization reaction forms a propylene homopolymer or a propylene copolymer. Optionally, one or more olefin monomers can be introduced into a polymerization reactor along with the propylene to react with the procatalyst, cocatalyst, and EED and to form a polymer, or a fluidized bed of polymer particles. Nonlimiting examples of suitable olefin monomers include ethylene, $C_{4-20}$ α-olefins, such as 1-butene, 1-pentene, 1-hexene, 4-methyl-1-pentene, 1-heptene, 1-octene, 1-decene, 1-dodecene and the like.

In an embodiment, the polymerization process may include a pre-polymerization step and/or a pre-activation step.

In an embodiment, the process includes mixing the external electron donor with the procatalyst composition. The external electron donor can be complexed with the cocatalyst and mixed with the procatalyst composition (pre-mixed) prior to contact between the catalyst composition and the olefin. In another embodiment, the external electron donor can be added independently to the polymerization reactor.

In an embodiment, the process includes forming a propylene-based polymer (propylene homopolymer or propylene copolymer) containing the BMPD. The propylene-based polymer has one or more of the following properties:

a melt flow rate (MFR) from about 0.01 g/10 min to about 800 g/10 min, or from about 0.1 g/10 min to about 200 g/10 min, or from about 0.5 g/10 min to about 150 g/10 min;

a xylene solubles content from about 0.1 wt % to about 11 wt %, or from about 0.1 wt % to about wt %, or from about 0.1 wt % to about 4 wt %, or from 0.1 wt % to less than 2.5 wt %;

a polydispersity index (PDI) from about 3.8 to about 15.0, or from about 4.0 to about 10, or from about 4.0 to about 8.0; and/or particles thereof with a bulk density greater than 0.28 g/cc to about 0.50 g/cc.

The propylene-based polymer may comprise two or more embodiments disclosed herein.

In an embodiment, the procatalyst composition and/or the polymer produced therefrom are/is phthalate-free or are/is otherwise void or devoid of phthalate and derivatives thereof.

The disclosure provides another process. In an embodiment, a process is provided and includes forming a liquid BMPD product and adding, under reaction conditions, the liquid BMPD product to a procatalyst precursor, a halogenating agent, and chlorobenzene to form a solid procatalyst composition. The process further includes contacting an olefin, under polymerization conditions, with the solid procatalyst composition, a cocatalyst, and an external electron donor and forming an olefin-based polymer.

In an embodiment, the olefin is propylene. The process includes forming a propylene homopolymer polymer having a xylene solubles content from 0.5 wt %, or 0.8 wt %, or 1.0 wt %, to 6.0 wt %, or 5.5 wt %, or 5.0 wt %, or 4.5 wt %, or 4.0 wt %.

In an embodiment, the olefin is propylene and ethylene. The process includes forming a propylene/ethylene copolymer having 0.5 wt % to 0.6 wt % units derived from ethylene and a xylene solubles content from 3.5 wt % to 3.8 wt %.

In an embodiment, the olefin is propylene and ethylene. The process includes forming a propylene/ethylene copolymer having 3.2 wt % units derived from ethylene and a xylene solubles content from 4.8 wt % to 5.9 wt %.

In an embodiment, the olefin is propylene and ethylene. The process includes forming a propylene/ethylene copolymer having 5.7 wt % units derived from ethylene and a xylene solubles content of 10.5 wt %.

In an embodiment, the olefin is propylene. The process includes forming particles of a propylene homopolymer, the particles having a bulk density from 0.27 g/cm$^3$ (18 lbs/ft$^3$) to 0.42 g/cm$^3$ (26 lbs/ft$^3$).

DEFINITIONS

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range. Numerical ranges have been recited, as discussed herein, reference melt index, melt flow rate, and other properties.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 and 20 carbon atoms.

The term "aryl," as used herein, refers to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. The aryls have 1 and 20 carbon atoms.

The term "composition," as used herein, includes a mixture of materials which comprise the composition, as well as reaction products and decomposition products formed from the materials of the composition.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

The term "ethylene-based polymer," as used herein, refers to a polymer that comprises a majority weight percent polymerized ethylene monomer (based on the total amount of polymerizable monomers), and optionally may comprise at least one polymerized comonomer.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term, "propylene-based polymer," as used herein, refers to a polymer that comprises a majority weight percent polymerized propylene monomer (based on the total amount of polymerizable monomers), and optionally may comprise at least one polymerized comonomer.

The term "substituted alkyl," as used herein, refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, haloalkyl, hydroxy, amino, phosphido, alkoxy, amino, thio, nitro, and combinations thereof. Suitable substituted alkyls include, for example, benzyl, trifluoromethyl and the like.

The term "substituted phenylene aromatic diester" includes substituted 1,2-phenylene aromatic diester, substituted 1,3-phenylene aromatic diester, and substituted 1,4- phenylene aromatic diester. In an embodiment, the substituted phenylene diester is a 1,2-phenylene aromatic diester with the structure (A) below:

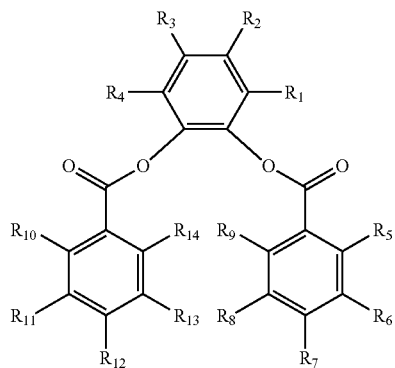

wherein $R_1$-$R_{14}$ are the same or different. Each of $R_1$-$R_{14}$ is selected from a hydrogen, substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. At least one of $R_1$-$R_{14}$ is not hydrogen.

Test Methods $^1$H nuclear magnetic resonance (NMR) data is obtained via a Brüker 400 MHz spectrometer in $CDCl_3$ (in ppm).

Melt flow rate (MFR) is measured in accordance with ASTM D 1238 test method and 230° C. with a 2.16 kg weight for propylene based polymer.

Bulk density is determined in accordance with ASTM D 1895 procedure B, and is measured as follows:

a. Fill a 4 oz tin can (about 30 grams) with polymer sample.

b. Pour resin through funnel into a pre-weighed metal cup (201 g/100 cc) until resin overfills the cup.

c. Level off the resin to the top of the cup using a large spatula. Do not shake the cup or pack the polymer in.

d. Weigh the cup with the polymer and subtract the weight of the cup.

e. The bulk density=g polymer/100 cc.

Xylene Solubles (XS) is the weight percent of resin (based on the total weight of the resin) that stays in the solution after the resin is dissolved in hot xylene and the solution is allowed to cool to 25° C. XS is measured using a $^1$H NMR method as described in U.S. Pat. No. 5,539,309, the entire content of which is incorporated herein by reference. XS may also be measured by flow injection polymer analysis using a Viscotek ViscoGEL H-100-3078 column with THF mobile phase flowing at 1.0 ml/min. The column is coupled to a Viscotek Model 302 Triple Detector Array, with light scattering, viscometer and refractometer detectors operating at 45° C. Instrument calibration is maintained with Viscotek PolyCAL™ polystyrene standards.

By way of example, and not limitation, examples of the present disclosure are provided.

EXAMPLES

A. BMPD

Comparative Sample 1

BMPD is prepared and purified according to the flowchart shown in FIG. 1 and is designated "refined BMPD."

Example 1

Figure 2:
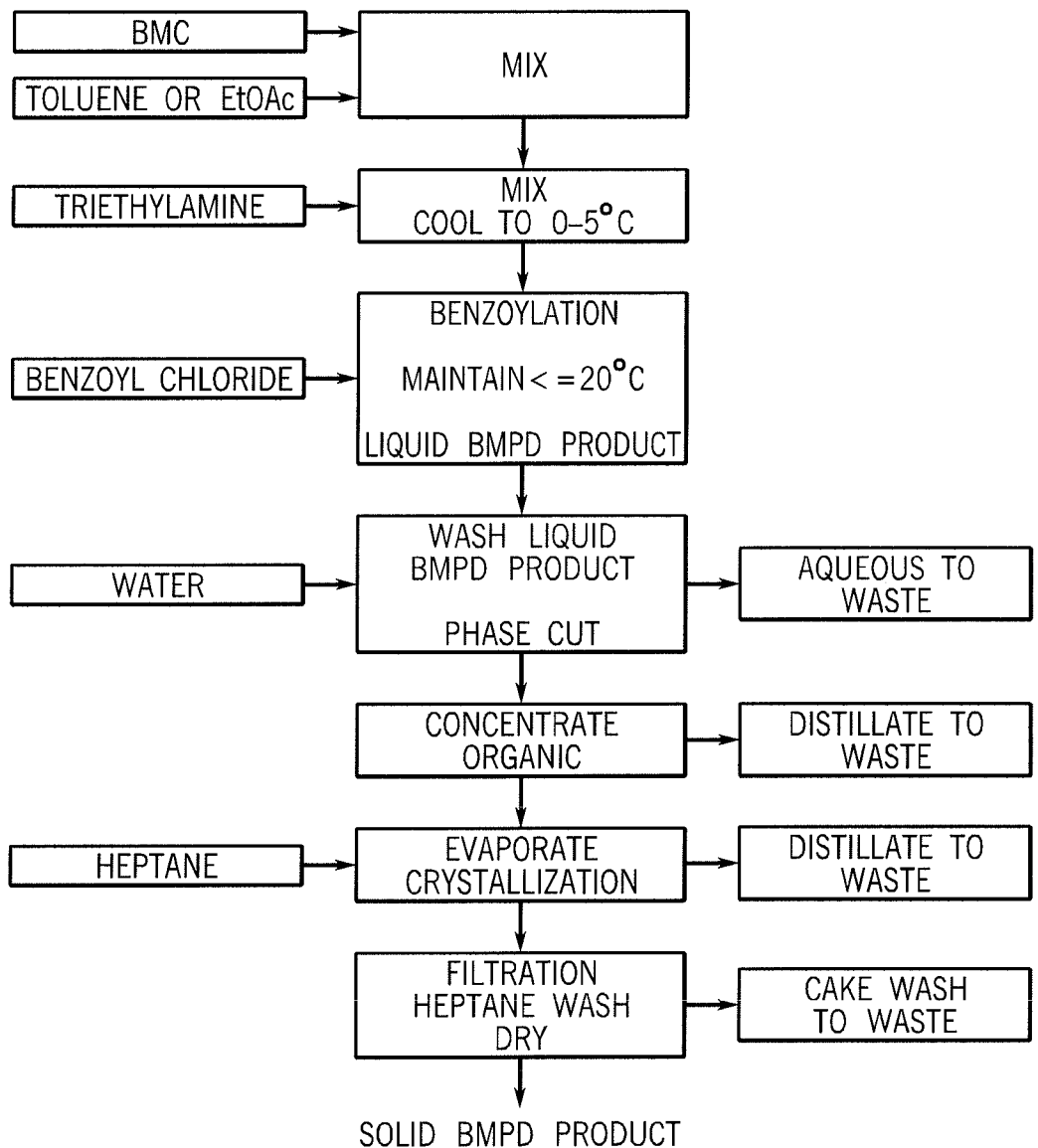
FIG. 2 is a flowchart showing a process for producing BMPD in accordance with an embodiment of the present disclosure.
Figure 3:
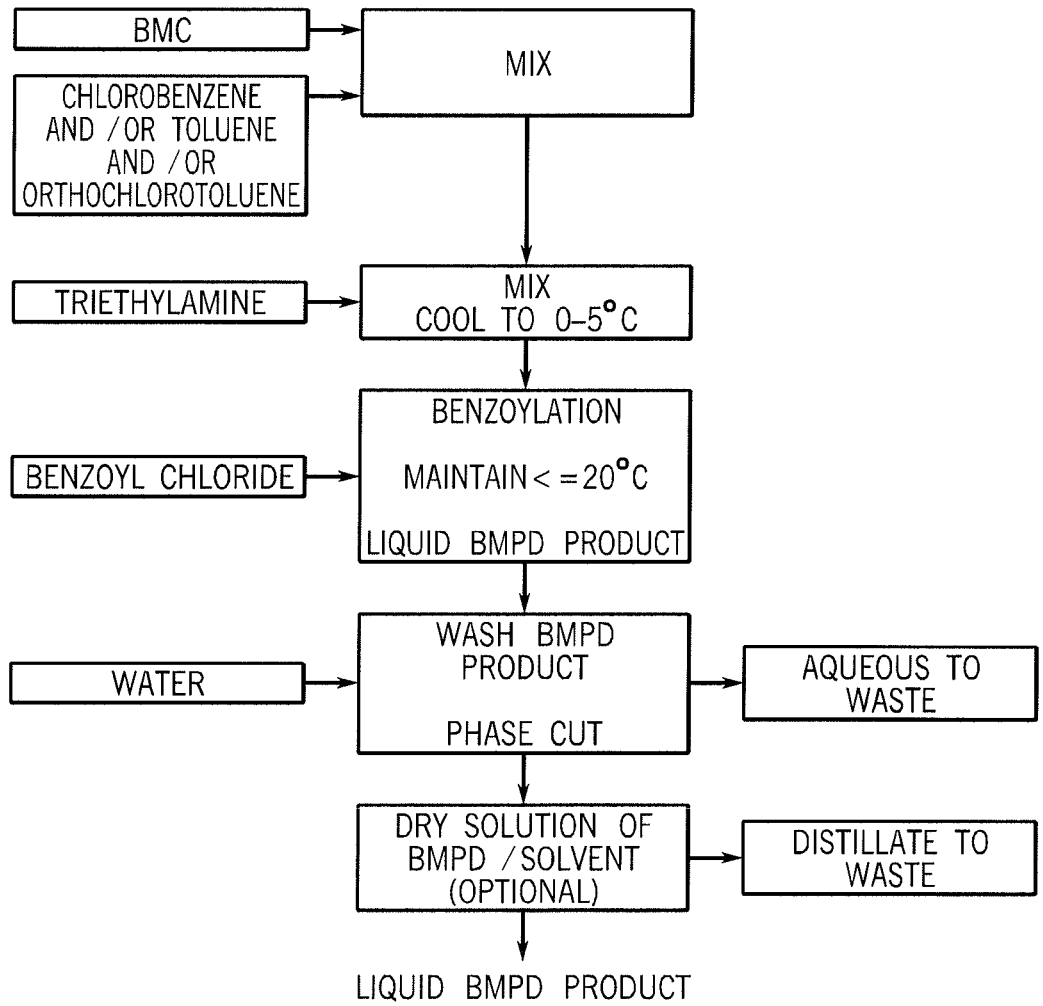
FIG. 3 is a flowchart showing a process for producing BMPD in accordance with an embodiment of the present disclosure.

Liquid BMPD product is prepared from toluene and concentrated to solid according to the flowchart shown in FIG. 2 and is designated as "BMPD/T."

Example 2

Liquid BMPD product is prepared from ethyl acetate and concentrated to solid according to the flowchart shown in FIG. 2 and is designated as "BMPD/EtOAc."

Example 3

Liquid BMPD product is prepared in chlorobenzene according to the flowchart shown in FIG. 3 and is designated as "BMPD/CB."

B. Catalyst Composition

Each of the four BMPD samples above is used as an internal electron donor in a respective procatalyst composition. The solid BMPD samples prepared in Examples 1 and 2 (above) are dissolved in chlorobenzene (CB) to 0.88 M solution. The BMPD solution of Example 3 is used as prepared.

The procatalyst compositions are prepared in fritted vessels that are stirred and electrically heated. 60 ml of 50 vol % $TiCl_4$/CB are added to the vessels at room temperature. Three grams of 27-µm MagTi precursor are added to the solution during stirring forming a slurry, and after two minutes the slurry is heated to 100° C. over a 50 minute period. A solution containing 1.03 grams of BMPD is added to the slurry when the temperature reaches 75° C. The reaction proceeds at 100° C. for 60 minutes, after which the first hot step is terminated by draining the solvent through the bottom of the fit in the absence of stirring.

An additional 60 ml of $TiCl_4$/CB are then added and the stirring is resumed. A solution containing 0.47 grams of BMPD donor is added. The slurry is heated to 115° C. and held for 30 minutes, and then filtered again (second hot step).

For the third hot step, 60 ml of $TiCl_4$/CB solution is added and the slurry is heated to 115° C. for 30 minutes. After the third filtration of $TiCl_4$/CB, the solid catalyst is rinsed and filtered three times at room temperature with 60 ml of isooctane. The wet catalyst cake is then dried to a free flowing powder under a nitrogen flow. The dry powder procatalyst composition is dispersed to a 5 wt % slurry in mineral oil for storage and handling.

C. Polymerization

Each of the four procatalyst compositions are polymerized in liquid propylene. The catalyst productivity and polymer xylene solubles (a measure of stereoregularity in the polymer) and settled bulk density obtained with the catalysts prepared by alternate routes (FIGS. 2-3) and from the original method are comparable to those prepared from the original method with full purification (refined BMPD) (FIG. 1).

Liquid propylene is polymerized under reaction conditions in a 1-gallon autoclave reactor. Each procatalyst composition is polymerized in liquid propylene in a 1-gallon autoclave. The reactor is charged with 1375 g of propylene and 3000 standard cm$^3$ of hydrogen and brought to 62° C. The procatalyst composition in the amount of 0.10 ml of 5-wt % slurry is precontacted with 7.2 ml of 0.27-M triethyl aluminum in isooctane and with 20 µl of dicyclopentyldimethoxysilane for 20 minutes to form the catalyst composition. The catalyst composition is then injected into the reactor at 62° C. to initiate polymerization. All catalyst components are flushed into the reactor with isooctane using a high-pressure catalyst injection pump. After the exotherm, the temperature is controlled to 67° C. for the duration of the one-hour runs.

The reaction of BMC and BC with the triethylamine scavenger creates byproducts in the desired BMPD product. It was expected that removal of reaction byproducts would require extensive purification in order to recover a BMPD grade of sufficient purity to be used in procatalyst production. However, it is unexpectedly discovered that the BMPD recovery process is simplified (resulting in shorter production times, lower raw material costs, and less waste generation) by way of the liquid BMPD product with the use of the water insoluble solvent.

Furthermore, the BMPD production can take place in solvents that can be directly used in the production of the procatalyst composition. Direct addition of the liquid BMPD product advantageously eliminates process steps by avoiding the need to crystallize and separate the BMPD as a solid.

Figure 4:
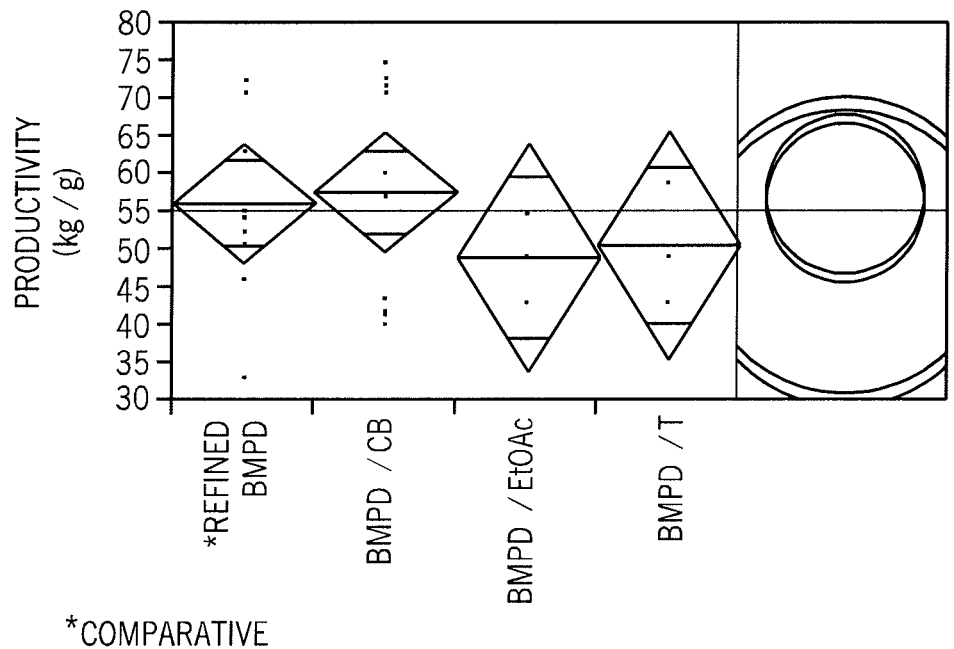
FIG. 4 is a graph showing catalyst productivity for catalysts containing BMPD, the BMPD produced by way of different processes.

FIG. 4 shows catalyst efficiency (productivity). The productivity for catalyst compositions containing BMPD made by way of procedures of Examples 1-3 exhibit catalyst efficiency from 41 kg/g to 53 kg/g.

Figure 5:
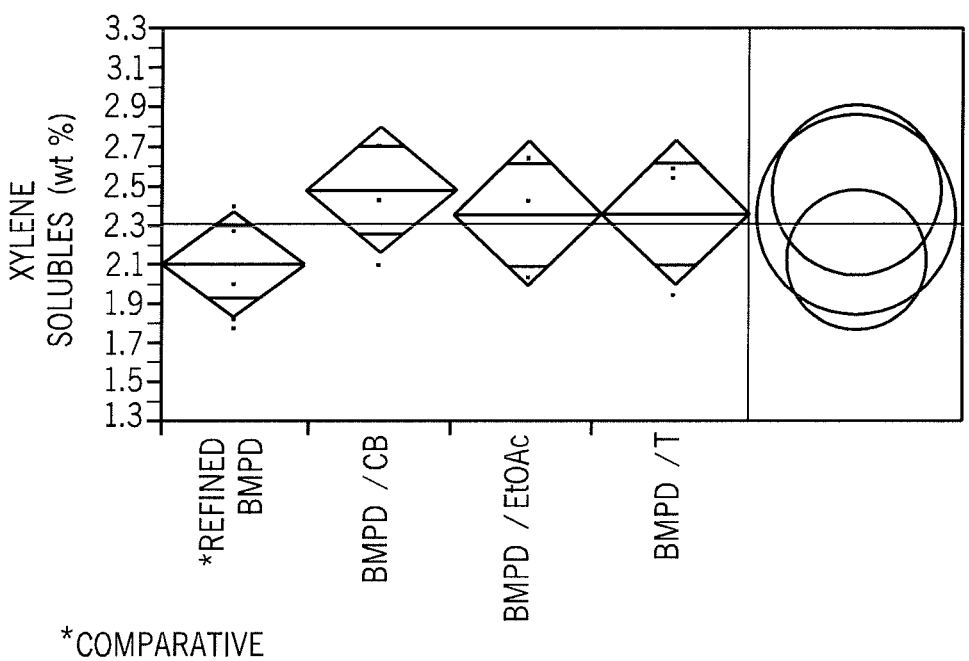
FIG. 5 is a graph showing xylene solubles for propylene-based polymers produced by catalysts containing BMPD, the BMPD produced by different processes.

FIG. 5 shows xylene solubles content for propylene homopolymer made from catalysts containing BMPD produced by way of the procedures of comparative sample 1 and Examples 1-3. For propylene homopolymer made by way of Examples 1-3, the average xylene solubles content is from 2.1 wt % to 2.5 wt %.

Figure 6:
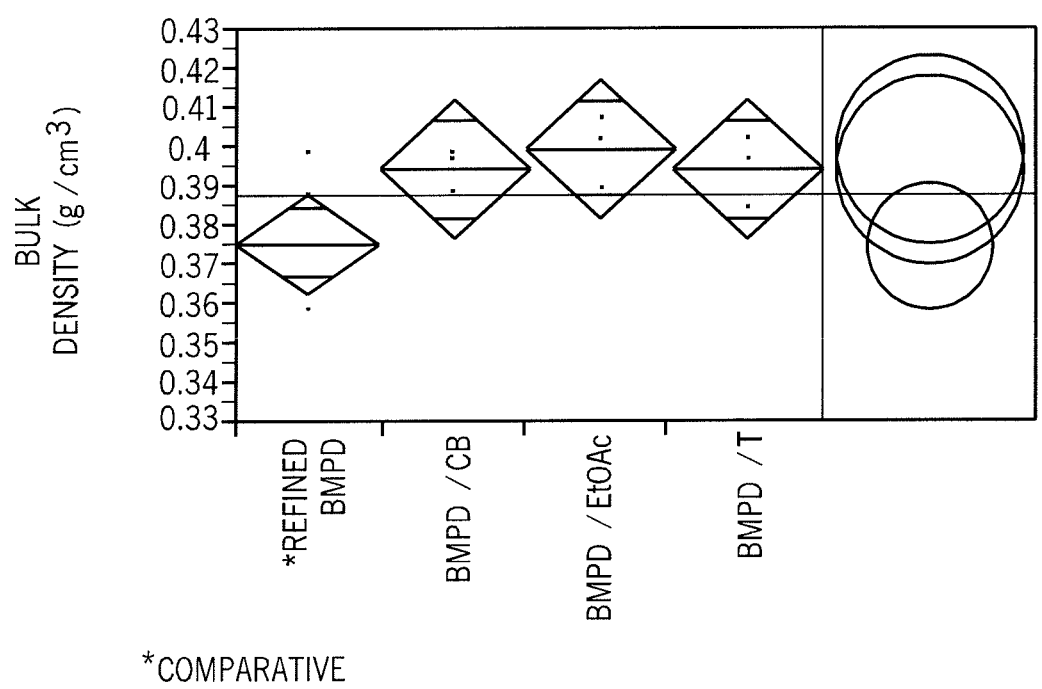
FIG. 6 is a graph showing the bulk density of propylene-based polymer particles produced from catalysts containing BMPD, the BMPD produced by different processes.

FIG. 6 shows polymer settled bulk density for polymers made from catalysts containing BMPD produced by way of the procedures of comparative sample 1 and Examples 1-3. The average settled bulk density for propylene homopolymer made by way of Examples 1-3 is from 0.375 g/cm$^3$ to 0.40 g/cm$^3$.

It is specifically intended that the present disclosure not be limited to the embodiments and illustrations contained herein, but include modified forms of those embodiments including portions of the embodiments and combinations of elements of different embodiments as come within the scope of the following claims.

What is claimed is:

1. A process comprising:
   (A) combining, under reaction conditions in a reaction mixture, 5-tert-butyl-3-methyl catechol (BMC), triethylamine, benzoyl chloride, and a water insoluble solvent having a water solubility of up to 0.5 g/L at 20° C. selected from the group consisting of chlorobenzene, orthochlorotoluene, and combinations thereof;
   (B) forming a liquid 5-tert-butyl-3-methyl-1,2-phenylene dibenzoate (BMPD) product that is dissolved in the water insoluble solvent;
   (C) introducing water into the reaction mixture to quench the reaction and washing with the introduced water the liquid BMPD that is dissolved in the water insoluble solvent to form a phase-separated solution of an aqueous phase and a nonaqueous phase;
   (D) maintaining the BMPD as a liquid in the water insoluble solvent of the reaction mixture before and during the water wash; and
   (E) separating the aqueous phase from the nonaqueous phase to form a washed BMPD product which is liquid and dissolved in the water insoluble solvent.

2. The process of claim 1 comprising contacting the liquid BMPD with a procatalyst precursor.

3. A process comprising:
   (A) combining, under reaction conditions in a first reaction mixture, a water insoluble solvent having a water solubility of up to 0.5 g/L at 20° C. selected from the group consisting of chlorobenzene, orthochlorotoluene, and combinations thereof, 5-tert-butyl-3-methyl catechol (BMC), triethylamine, and benzoyl chloride;
   (B) forming a liquid 5-tert-butyl-3-methyl-1,2-phenylene dibenzoate (BMPD) product;
   (C) introducing water into the reaction mixture to quench the reaction and washing with the introduced water, the liquid BMPD product and maintaining the BMPD product as a liquid in the water insoluble solvent of the first reaction mixture before and during the wash;
   (D) allowing the reaction mixture to phase-separate into a water phase and non-aqueous phase;
   (E) separating the water phase from the non-aqueous phase to obtain a washed liquid BMPD product;
   (F) adding, under reaction conditions, the washed liquid BMPD product with the water insoluble solvent to a second reaction mixture comprising a procatalyst precursor, a halogenating agent, and chlorobenzene; and
   (G) forming a solid procatalyst composition.

4. The process of claim 3 comprising adding to the first reaction mixture the water insoluble solvent orthochlorotoluene.

5. The process of claim 3 comprising adding to the first reaction mixture the water insoluble solvent chlorobenzene.

6. The process of claim 3 comprising directly adding the first reaction mixture to the second reaction mixture.

7. A process comprising:
   (A) adding, under reaction conditions, the liquid BMPD product with water insoluble solvent of claim 1 to a procatalyst precursor, a halogenating agent, and chlorobenzene to form a solid procatalyst composition;
   (B) contacting an olefin, under polymerization conditions, with the solid procatalyst composition, a cocatalyst, and an external electron donor; and
   (C) forming an olefin-based polymer.

8. The process of claim 7 comprising forming the liquid BMPD product in the solvent orthochlorotoluene.

9. The process of claim 7 wherein the olefin is propylene, the process comprising forming a propylene homopolymer having a xylene solubles content from 0.5 wt % to 6 wt %.

10. The process of claim 1 wherein the water insoluble solvent comprises chlorobenzene.

11. The process of claim 1 wherein the water insoluble solvent comprises orthochlorotoluene.

12. The process of claim 7 comprising forming the liquid BMPD product in the solvent chlorobenzene.

13. The process of claim 1 comprising concentrating the washed liquid BMPD product to form a solid BMPD product.

* * * * *